United States Patent
Tsujii et al.

(10) Patent No.: US 8,297,839 B2
(45) Date of Patent: Oct. 30, 2012

(54) RADIATION IMAGING APPARATUS AND METHOD FOR CONTROLLING RADIATION IMAGING APPARATUS

(75) Inventors: Osamu Tsujii, Kawasaki (JP); Hiroyuki Ichiyoshi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 221 days.

(21) Appl. No.: 12/790,589

(22) Filed: May 28, 2010

(65) Prior Publication Data

US 2010/0303207 A1   Dec. 2, 2010

(30) Foreign Application Priority Data

Jun. 2, 2009  (JP) .................... 2009-133382

(51) Int. Cl.
  *H05G 1/02* (2006.01)
  *H05G 1/64* (2006.01)
  *A61B 6/08* (2006.01)
(52) U.S. Cl. .................. 378/197; 378/98; 378/205
(58) Field of Classification Search .............. 378/98, 378/196, 197, 198, 4, 19, 205, 207, 62
See application file for complete search history.

(56) References Cited

U.S. PATENT DOCUMENTS

| | | | | |
|---|---|---|---|---|
| 4,358,856 A | * | 11/1982 | Stivender et al. | 378/167 |
| 4,807,273 A | * | 2/1989 | Haendle | 378/197 |
| 4,894,855 A | * | 1/1990 | Kresse | 378/196 |
| 6,200,024 B1 | * | 3/2001 | Negrelli | 378/197 |
| 6,325,537 B1 | * | 12/2001 | Watanabe | 378/197 |
| 6,592,259 B2 | * | 7/2003 | Crain et al. | 378/197 |
| 2006/0023830 A1 | * | 2/2006 | Schomberg | 378/4 |

FOREIGN PATENT DOCUMENTS

| | | |
|---|---|---|
| JP | 2000-116631 A | 4/2000 |
| JP | 2002-336220 A | 11/2002 |

* cited by examiner

*Primary Examiner* — Irakli Kiknadze
(74) *Attorney, Agent, or Firm* — Canon U.S.A., Inc. IP Division

(57) ABSTRACT

A radiation imaging apparatus includes a C-arm, a radiation source configured to irradiate a subject with radiation, and a two-dimensional detection device configured to detect the radiation having passed through the subject. The radiation source and the two-dimensional detection device are arranged to face each other across the C-arm, and at least one of the radiation source and the two-dimensional detection device is attached to the C-arm via a sub-arm that is rotatably connected to a frame of the C-arm.

13 Claims, 6 Drawing Sheets

RADIATION IMAGING APPARATUS AND METHOD FOR CONTROLLING RADIATION IMAGING APPARATUS

BACKGROUND OF THE INVENTION

1. Field of the Invention

The present invention relates to a radiation imaging apparatus, and a method for controlling the radiation imaging apparatus. Particularly, the present invention is well adaptable to an X-ray imaging apparatus with a C-arm used in an operating room.

2. Description of the Related Art

An X-ray imaging apparatus with a C-arm used in an operating room is required to be capable of freely imaging a portion of a patient to be operated, and to be capable of executing a computed tomography (CT) with the rotation at an angle of 180 degrees. In recent years, a function has been demanded from such an imaging apparatus in which an imaging distance can be changed to be short without fixing the imaging distance for reducing the X-ray exposure to a patient and operator.

For example, in an X-ray diagnostic apparatus discussed in Japanese Patent Application Laid-Open No. 2000-116631, a multi-joint arm is coupled to an end of a C-arm to allow an X-ray planar detection device to move within the internal space of the C-arm so as to freely image a subject from a multitude of directions without sliding the C-arm. Japanese Patent Application Laid-Open No. 2000-116631 also discusses a link mechanism that movably holds the X-ray planar detection device to the C-arm.

The X-ray diagnostic apparatus discussed in Japanese Patent Application Laid-Open No. 2000-116631 can freely image the portion of a patient to be imaged, and enables CT in which the apparatus rotates at an angle of 180 degrees. However, the multi-joint arm that is linked to the end portion of the C-arm represents a problem in that it is difficult to control the multi-joint arm to position the X-ray planar detection device at the desired imaging angle. That is, when the X-ray tube is arranged to face the X-ray planar detection device, the multi-joint becomes a hindrance since it occupies a large space within the C-arm.

An X-ray diagnostic apparatus discussed in Japanese Patent Application Laid-Open No. 2002-336220 includes an X-ray tube, an X-ray detection device, a grid portion arranged on an image-receiving surface of the X-ray detection device, and an arm supporting the X-ray tube and the X-ray detection device to be capable of changing the distance between the X-ray tube and the X-ray detection device.

The X-ray diagnostic apparatus discussed in Japanese Patent Application Laid-Open No. 2002-336220 can change the distance between the X-ray source and the two-dimensional detection device without changing the imaging axis. However, when the length of the distance to be changed increases, the slide mechanism for changing the length increases, which arises a problem of substantially increasing the outer dimension of the C-arm. When the outer dimension of the C-arm increases, the apparatus is difficult to be used in an operating room having a small work area.

SUMMARY OF THE INVENTION

The present invention is directed to a radiation imaging apparatus having a C-arm and a control method of the radiation imaging apparatus capable of effectively utilizing the space in the C-arm and capable of enhancing usability of the radiation imaging apparatus by an operator.

According to an aspect of the present invention, a radiation imaging apparatus includes a C-arm, a radiation source configured to irradiate a subject with radiation, and a two-dimensional detection device configured to detect the radiation having passed through the subject, wherein the radiation source and the two-dimensional detection device are arranged to face each other across the C-arm, and wherein at least one of the radiation source and the two-dimensional detection device is attached to the C-arm via a sub-arm that is rotatably connected to a frame of the C-arm at the inside from the end portion of the frame.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1A:
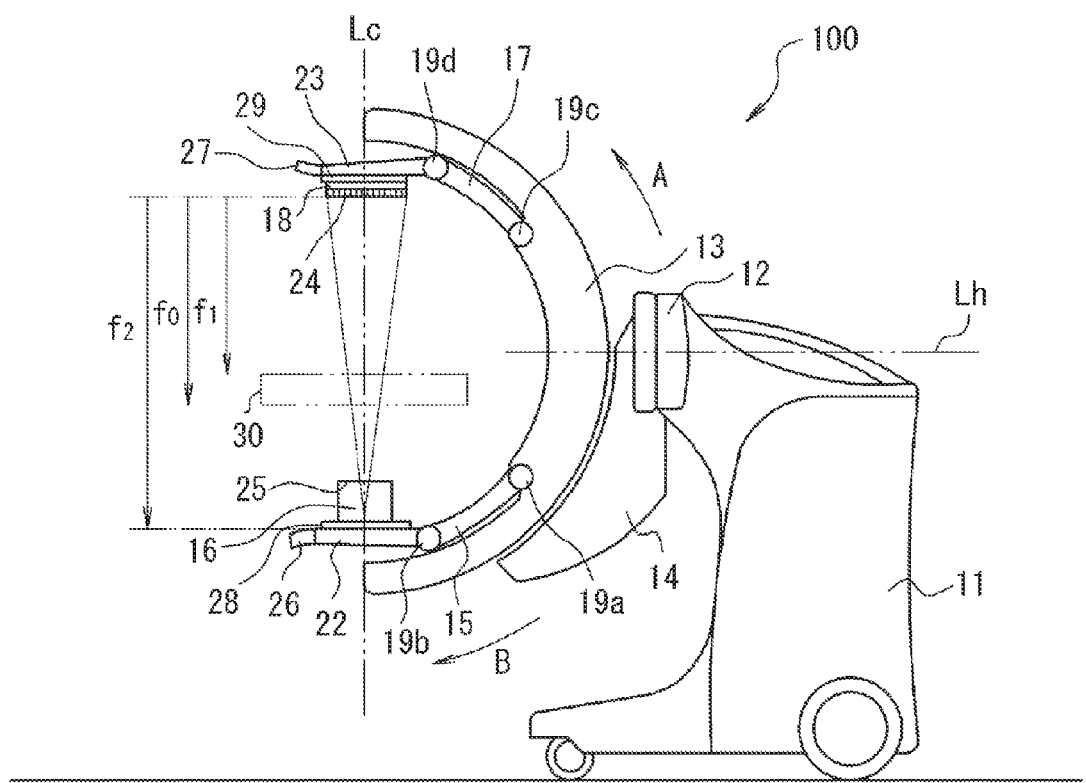
FIGS. 1A and 1B illustrate a configuration of a radiation imaging apparatus.
Figure 1B:
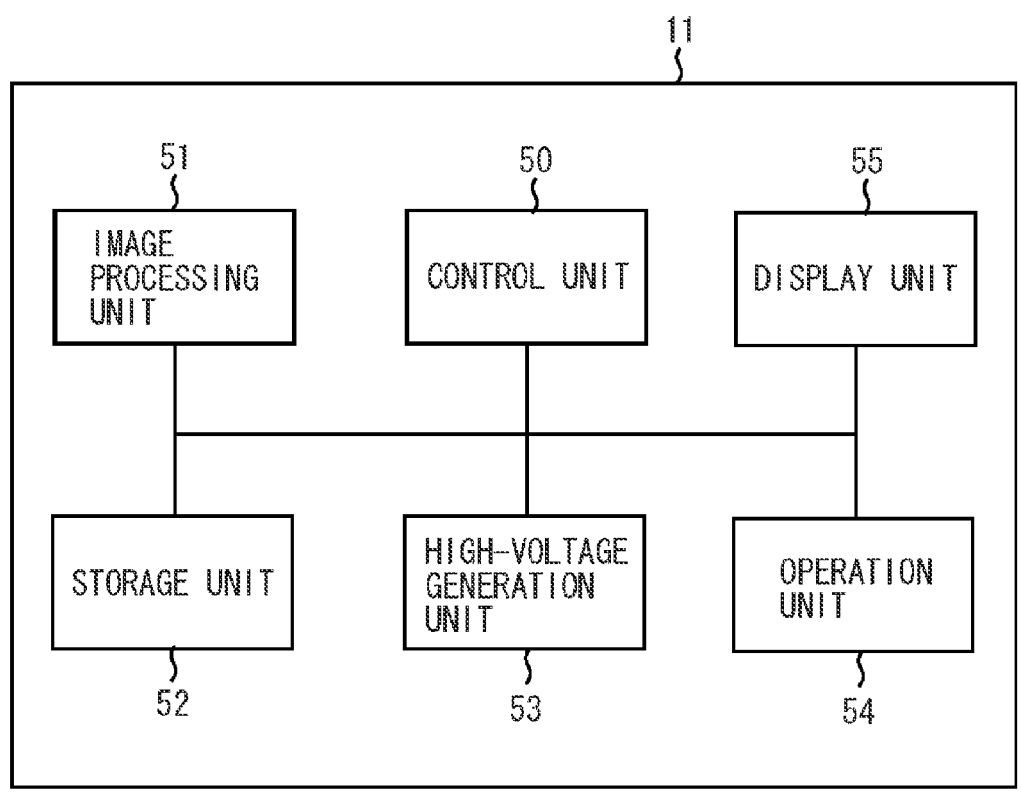

An X-ray imaging apparatus is taken as an example of the radiation imaging apparatus in the present exemplary embodiment. However, embodiments of the present invention or modifications thereof may be applicable to other imaging apparatuses capable of radiating an object or subject with electromagnetic radiation or subatomic particles and configured to detect the radiation having passed through the object or subject. FIG. 1A is a side view illustrating an outer appearance of the X-ray imaging apparatus. FIG. 1B is a diagram illustrating the configuration of a main body of the X-ray imaging apparatus.

As illustrated in FIG. 1A, the X-ray imaging apparatus 100 has a main body 11. The main body 11 of the X-ray imaging apparatus 100 is provided with a rotation support portion 12 that supports a slide support portion 14. The slide support portion 14 can rotate about the rotation support portion 12 to a rotation shaft Lh in the horizontal direction indicated by a two-dot-chain line in FIG. 1A.

Figure 2A:
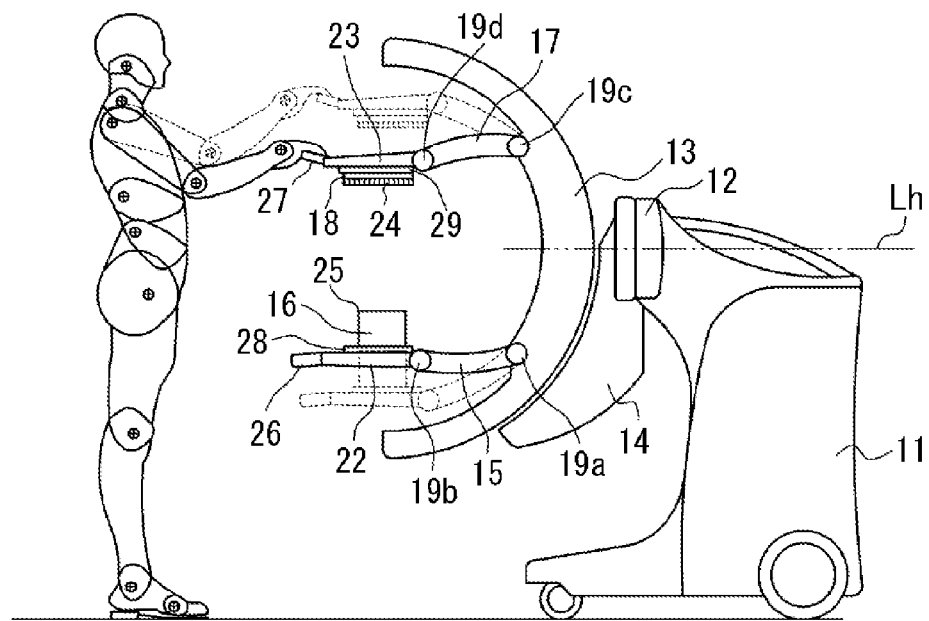
FIGS. 2A and 2B are side views illustrating when an X-ray tube and a two-dimensional detection device are moved.
Figure 2B:
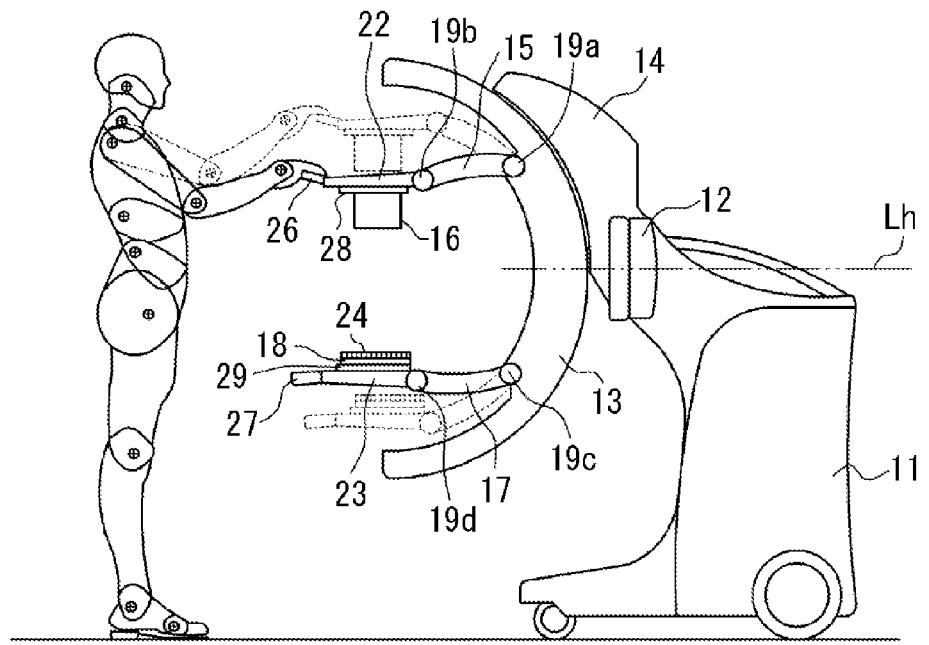

The slide support portion 14 in the present exemplary embodiment can rotate about the rotation support portion 12 within a rotation angle of about 180 degrees. When the slide support portion 14 is rotated about the rotation support portion 12 at an angle of 180 degrees, the end portions of a semicircular C-arm 13 are exchanged as illustrated in FIG. 2B.

A bed 30 for a subject (patient) is arranged between the end portions of the C-arm 13. When the C-arm 13 is rotated at 180 degrees, an imaging method (under-tube), in which an X-ray is generated from the back of the subject who is in the supine position, and an imaging method (over-tube), in which an X-ray is generated from the front of the subject who is in the supine position, can be executed.

The slide support portion 14 supports the C-arm 13 in such a manner that the C-arm 13 can slide along the shape of the frame of the C-arm 13 in a direction indicated by an arrow A or a direction indicated by an arrow B in FIG. 1A, so as to trace a substantially semicircular path concentric to the C-arm 13. The slide angle of the slide support portion 14 is set to the angle capable of executing CT imaging.

Specifically, the slide angle is desirably set to the angle obtained by adding an X-ray fan angle to 180 degrees, i.e., not less than 180 degrees. The fan angle means the spread of the X-ray emitted from an X-ray tube 16 in the horizontal direction. When the CT is not needed, the slide angle may be set to 180 degrees.

Accordingly, the C-arm 13 slides at least in the A direction at 90 degrees or in the B direction at 90 degrees from the state illustrated in FIG. 1A. Since the C-arm 13 slides to the slide support portion 14, the subject can be imaged from both sides of the subject who is in the supine position or in the recumbent position.

The X-ray tube 16 serving as a radiation source is arranged at one end portion of the frame of the C-arm 13 through a first sub-arm 15. The first sub-arm 15 is pivotably connected by a first joint 19a. The first joint 19a is provided at the portion on the frame of the C-arm 13 inward from one end portion of the C-arm 13 and serves as a connection portion.

The first joint 19a is a rotation mechanism. The first joint 19a is, for example, a horizontally arranged link shaft. A tube mounting portion 22 serving as a mounting portion of the X-ray tube 16 is pivotably connected, through a second joint 19b, to the end portion of the first sub-arm 15 opposite to the first joint 19a. The second joint 19b is also a rotation mechanism, and it is, for example, a horizontally arranged link shaft.

The tube mounting portion 22 has a grip 26 that is used to move the X-ray tube 16 by an operator. The X-ray tube 16 is mounted on the tube mounting portion 22 through a below-described shift portion 28. As described above, the X-ray tube 16 serving as the radiation source is provided at one end portion of the frame of the C-arm 13 through the first sub-arm 15.

Since the first joint 19a and the second joint 19b are the horizontally arranged link shafts, the first sub-arm 15 and the X-ray tube 16 can move in the plane formed by the frame of the C-arm 13.

A two-dimensional detection device 18 that detects the X-ray, which is emitted from the X-ray tube 16 and passes through the subject, is arranged at the other end portion of the frame of the C-arm 13 through a second sub-arm 17. The second sub-arm 17 is pivotably connected by a third joint 19c, which is provided at the portion on the frame of the C-arm 13 inward from the other end portion of the C-arm 13 and which serves as a connection portion.

The third joint 19c is a rotation mechanism. The third joint 19c is, for example, a horizontally arranged link shaft. A detection device mounting portion 23 serving as a mounting portion of the two-dimensional detection device 18 is pivotably connected, through a fourth joint 19d, to the end portion of the second sub-arm 17 opposite to the third joint 19c.

The fourth joint 19d is a rotation mechanism, and it is, for example, a horizontally arranged link shaft. The detection device mounting portion 23 has a grip 27 that is used to move the two-dimensional detection device 18 by an operator. The two-dimensional detection device 18 is mounted on the detection device mounting portion 23 through a below-described shift portion 29. As described above, the two-dimensional detection device 18 that detects the X-ray emitted from the X-ray tube 16 is provided at the other end portion of the frame of the C-arm 13 through the second sub-arm 17.

Since the third joint 19c and the fourth joint 19d are the horizontally arranged link shafts, the second sub-arm 17 and the two-dimensional detection device 18 can move in the plane formed by the frame of the C-arm 13.

With this configuration, the X-ray tube 16 and the two-dimensional detection device 18 are arranged to face each other at both end portions of the C-arm 13 across the bed 30 of the subject indicated by a chain line in FIG. 1A.

The configuration of the main body 11 of the X-ray imaging apparatus 100 will be described with reference to FIG. 1B. As illustrated in FIG. 1B, the main body 11 includes a control unit 50, an image processing unit 51, a storage unit 52, a high-voltage generation unit 53, an operation unit 54, and a display unit 55. The control unit 50 controls the overall operation of the X-ray imaging apparatus 100. Specifically, the control unit 50 executes a program stored in the storage unit 52 according to a selection of a mode.

The image processing unit 51 converts the X-ray data detected by the two-dimensional detection device 18 into image data that can be confirmed or stored by the operator. The storage unit 52 is a large-capacity storage medium and a memory such as a random access memory (RAM) or a read-only memory (ROM). The storage unit 52 stores the program according to the mode, or is used as a work memory by the control unit 50.

The high-voltage generation unit 53 supplies high voltage to the X-ray tube 16. The operation unit 54 includes various operation switches. The display unit 55 is a display on which the image data converted by the image processing unit 51 is displayed.

The rotation angle of the first sub-arm 15 and the second sub-arm 17 will next be described.

The rotation angles of the first sub-arm 15 and the second sub-arm 17 are determined according to various factors. The factors include, for example, the grid portion 24 arranged on the front surface (image-receiving surface) of the two-dimensional detection device 18, the X-ray diaphragm 25 arranged at the front surface of the X-ray tube 16, the relationship between the diameter of the frame of the C-arm 13 and the lengths of the respective sub-arms, etc.

The grid portion 24 arranged at the front surface of the two-dimensional detection device 18 has a function of eliminating (e.g., blocking, absorbing or deflecting) scattered rays of the X-ray, for example, by cutting off diagonally incident X-rays. The grid portion 24 has a thin lead plate with strips arranged thereon at a constant distance. More specifically, there are various types of grids (e.g., focused, parallel, criss-crossed, etc) that may be used as the grid portion 24. Each type of grid can determine certain aspect (e.g., grid ratio, grid density, focal range, etc) of the grid portion 24. In a focused grid, for example, strips of radiation-absorbing material are arranged at a predetermined distance from each other and tilted progressively from the center to the outer edge thereof. Radiation rays passing through each of these strips converge at a point known as the grid focus. For optimal imaging, it is desirable that the grid focus substantially matches the distance between the focal point of the X-ray generation portion and the detecting surface (SID) of the X-ray detection device.

When the convergent distance of the grid portion is defined as f0 as illustrated in FIG. 1A, the limit of the usage distance of the grid portion 24 is set to include the convergent distance f0 within a usable range thereof. When the lower limit of the usage distance is defined as f1, and the upper limit of the usage distance is defined as f2, the equation of f1=<f0=<f2 is established.

The X-ray photography cannot be executed with the X-ray tube 16 and the two-dimensional detection device 18 being made closer to each other with the distance shorter than the lower limit f1 or higher than the upper limit f2 of the usage distance of the grid portion 24. Therefore, the first to fourth joints 19a to 19d regulate the rotation, through the first sub-arm 15, the second sub-arm 17, the tube mounting portion 22, and the detection device mounting portion 23, to prevent the distance between the X-ray tube 16 and the two-dimensional detection device 18 from being shorter than the lower limit f1 of the usage distance.

The X-ray diaphragm 25 arranged at the front surface of the X-ray tube 16 regulates the X-ray irradiation range to irradiate only the portion needed for the diagnosis, which prevents the subject from being unnecessarily exposed to the radiation. On the other hand, the X-ray diaphragm 25 increases the X-ray irradiation range to be capable of observing the portion needed for the diagnosis at a time. Therefore, the limit of the near distance between the X-ray tube 16 and the two-dimensional detection device 18 is determined in the minimum area or the maximum area that can be set by the X-ray diaphragm 25.

As described above, the rotation angles of the first to fourth joints 19a to 19d are determined by the characteristic of the grid portion 24 or the X-ray diaphragm 25.

In the above description, the first sub-arm 15 and the second sub-arm 17 are moved in the plane formed by the frame of the C-arm 13. However, the present invention is not limited thereto. For example, it can be configured so that the first sub-arm 15 and the second sub-arm 17 can be moved in the direction substantially perpendicular to the plane formed by the frame of the C-arm 13.

In this case, a fifth joint and a sixth joint, which allow the respective sub-arms to pivot in the direction perpendicular to the plane, may be added between the C-arm 13 and the respective sub-arms.

This configuration can easily move the imaging area on the subject in the body axis of the subject. Specifically, the X-ray tube 16 and the two-dimensional detection device 18 can be moved in the body axis direction of the subject, whereby the operator can easily execute X-ray photography without moving the main body 11.

The case in which the distance between the X-ray tube 16 and the two-dimensional detection device 18 is changed, i.e., in which the imaging distance is changed, will next be described. A brake release switch (not illustrated) is provided at the position proximate to the grips 26 and 27 at the end of the tube mounting portion 22 and at the end of the detection device mounting portion 23.

When the operator presses the brake release switch while gripping the grip 27 at the two-dimensional detection device 18, for example, the brake of the rotation mechanism made of the third joint 19c and the fourth joint 19d can be released. When the operator grips the grip 27 with the brake being released, and moves the two-dimensional detection device 18 close to the X-ray tube 16 as illustrated in FIG. 2A, the imaging distance can be changed.

In the present exemplary embodiment, the imaging distance is changed based on the condition that the X-ray light flux from the X-ray tube 16 is not diagonally incident on the two-dimensional detection device 18, i.e., that the X-ray tube 16 and the two-dimensional detection device 18 move parallel to each other in such a manner that the front surface of the two-dimensional detection device 18 is always orthogonal to the imaging axis Lc illustrated in FIG. 1A. The imaging axis Lc is a line linking the focal point of the X-ray tube 16 and the center of the two-dimensional detection device 18.

The rotation angles of the third joint 19c and the fourth joint 19d can uniquely be determined through the parallel movement of the two-dimensional detection device 18 to allow the front surface of the two-dimensional detection device 18 to be always orthogonal to the imaging axis Lc. Therefore, the second sub-arm 17 and the detection device mounting portion 23 can easily be controlled.

The provision of the second sub-arm 17 can increase the space in the C-arm 13 when the imaging distance is increased or decreased. The detection device mounting portion 23 is not limited to be provided through the third joint 19c, the second sub-arm 17, and the fourth joint 19d. The detection device mounting portion 23 may be provided through two or more joints (rotation mechanism).

Similarly, the brake of the rotation mechanism by the first joint 19a and the second joint 19b can be released, when the operator press the brake release switch while gripping the grip 26 at the X-ray tube 16. When the operator grips the grip 26 with the brake being released, and moves the X-ray tube 16 close to the two-dimensional detection device 18 as illustrated in FIG. 2B, the imaging distance can be changed.

The rotation angles of the first joint 19a and the second joint 19b can uniquely be determined through the parallel movement of the X-ray tube 16 to allow the front surface of the two-dimensional detection device 18 to be always orthogonal to the imaging axis Lc. Therefore, the first sub-arm 15 and the tube mounting portion 22 can easily be controlled.

The provision of the first sub-arm 15 can increase the space in the C-arm 13 when the imaging distance is increased or decreased.

The tube mounting portion 22 is not limited to be provided through the first joint 19a, the first sub-arm 15, and the second joint 19b. The tube mounting portion 22 may be provided through two or more joints (rotation mechanism).

As described above, the X-ray light flux from the X-ray tube 16 is prevented from being diagonally incident on the two-dimensional detection device 18. Therefore, the grid portion 24 does not cut off the X-ray that is effective for the diagnosis, with the result that an effective X-ray photography can be carried out. There are two modes for the control of preventing the diagonal incidence of the X-ray light flux.

One of them is a mode (active-side control mode) for controlling the two-dimensional detection device 18 in such a manner that a vertical line to the front surface of the two-dimensional detection device 18 passes through the focal point of the X-ray tube 16 when the operator changes the imaging distance while holding the grip 27 of the detection device mounting portion 23. In the active-side control mode, when the operator changes the imaging distance while holding, in contrast, the grip 26 at the tube mounting portion 22, the X-ray tube 16 is controlled in such a manner that the vertical line to the front surface of the two-dimensional detection device 18 passes through the focal point of the X-ray tube 16.

The other one is a mode (passive-side control mode) for controlling the X-ray tube 16 in such a manner that a vertical line to the front surface of the two-dimensional detection device 18 passes through the focal point of the X-ray tube 16 when the operator changes the imaging distance while holding the grip 27 of the detection device mounting portion 23. In the passive-side control mode, when the operator changes the imaging distance while holding, in contrast, the grip 26 at the tube mounting portion 22, the two-dimensional detection device 18 is controlled in such a manner that the vertical line to the front surface of the two-dimensional detection device 18 passes through the focal point of the X-ray tube 16.

The merit of the active-side control mode is that the incident angle of the X-ray to the subject is easy to be kept when the detection device mounting portion 23 is moved. The merit of the passive-side control mode is that, when the operator moves the detection device mounting portion 23 while holding the grip 27, the operator does not feel torque from the second sub-arm 17 or other components. The above-mentioned two modes are switched by the control unit 50 according to the setting made by the operator when operating the operation unit 54.

The two-dimensional detection device 18 and the X-ray tube 16 in the present exemplary embodiment can move in conjunction with each other. More specifically, the X-ray imaging apparatus 100 can be configured such that the first sub-arm 15 automatically moves in conjunction with the second sub-arm 17. The second sub-arm 17 automatically moves in conjunction with the first sub-arm 15.

A mode changeover switch (not illustrated) is provided at the position proximate to either one of the grips 26 and 27. The operator can change the mode to a single mode or conjunction mode by the mode changeover switch.

In the single mode, only one of the sub-arms 15 and 17, which is at the side of the grips 26 or 27 that is held by the operator, and only one of the detection device mounting portion 23 and the tube mounting portion 22, which is at the side of the grips 26 or 27 that is held by the operator, move.

On the other hand, in the conjunction mode, one of the sub-arms 15 and 17, which is at the side of the grips 26 or 27 that is not held by the operator, and one of the detection device mounting portion 23 and the tube mounting portion 22, which is at the side of the grips 26 or 27 that is not held by the operator, also move in conjunction with the other sub-arm and the other mounting portion. The control unit 50 changes the mode between the single mode and the conjunction mode according to the setting of the mode changeover switch.

The conjunction mode includes two types of modes, which are a constant imaging-distance conjunction mode and a variable imaging-distance conjunction mode.

In the constant imaging-distance conjunction mode, the sub-arm 15 or 17 at the side of the grip 26 or 27 that is not held by the operator and the mounting portion at the side of the grip 26 or 27 that is not held by the operator move in conjunction with each other so as not to change the imaging distance. Specifically, in the constant imaging-distance conjunction mode, each of the sub-arms 15 and 17 and each of the mounting portions 22 and 23 move, respectively in conjunction with each other, to allow the imaging distance between the two-dimensional detection device 18 and the X-ray tube 16 to be constant.

For example, as the two-dimensional detection device 18, i.e., the second sub-arm 17, is moved away from the subject, the X-ray tube 16, i.e., the first sub-arm 15 moves close to the subject. In this case, the imaging area is decreased to be capable of increasing the magnification ratio of the subject without changing the aperture of the X-ray diaphragm 25 and the imaging distance.

On the other hand, as the two-dimensional detection device 18, i.e., the second sub-arm 17, is moved close to the subject, the X-ray tube 16, i.e., the first sub-arm 17, moves away from the subject. In this case, the imaging area is increased to be capable of decreasing the magnification ratio of the subject, but the imaging distance is maintained substantially constant.

In the variable imaging-distance conjunction mode, the sub-arm 15 or 17 at the side of the grip 26 or 27 that is not held by the operator and the mounting portion at the side of the grip 26 or 27 that is not held by the operator move in conjunction with each other so as to change the imaging distance. Specifically, in the variable imaging-distance conjunction mode, each of the sub-arms 15 and 17 and each of the mounting portions 22 and 23 move so that the two-dimensional detection device 18 and the X-ray tube 16 move in reverse direction with respect to each other.

For example, as the two-dimensional detection device 18, i.e., the second sub-arm 17, is moved away (to be apart) from the subject, the X-ray tube 16, i.e., the first sub-arm 15, is also moved away (to be apart) from the subject. In this case, the imaging area is changed with the magnification ratio being maintained substantially constant.

On the other hand, as the two-dimensional detection device 18, i.e., the second sub-arm 17, is moved towards (to be close to) the subject, the X-ray tube 16, i.e., the first sub-arm 17, is also moved towards (to be close to) the subject. In this case, the imaging area is changed with the magnification ratio being maintained substantially constant. Specifically, when the operator moves the two-dimensional detection device 18 from the position indicated by a broken line to the position indicated by a solid line in FIG. 2A as holding the grip 27, the X-ray tube 16 is moved from the position indicated by the broken line to the position indicated by the solid line.

The operation described above is controlled according to the instruction from the control unit 50. Specifically, when the control unit 50 detects the movement of the second sub-arm 17 (i.e., the rotation angle of the third joint 19c) at the side of the grip 27 held by the operator, the control unit 50 calculates the rotation angle for rotating the first joint 19a according to the detected rotation angle of the third joint 19c.

The first joint 19a rotates the first sub-arm 15 based on the calculated rotation angle of the third joint 19c. The second joint 19b rotates the tube mounting portion 22, i.e., the X-ray tube 16, according to the rotation angle of the first joint 19a. On the other hand, when the first sub-arm 15 is moved, the third joint 19c rotates the second sub-arm 17 based on the calculated rotation angle.

The fourth joint 19d rotates the detection device mounting portion 23, i.e., the two-dimensional detection device 18, according to the rotation angle of the third joint 19c. In this manner, the respective joints 19a to 19d move in conjunction the two-dimensional detection device 18 and the X-ray tube 16 in the reverse direction to make the distance variable, or move them simultaneously in the same direction to allow the imaging distance between the two-dimensional detection device 18 and the X-ray tube 16 to be constant.

The control unit 50 switches from the constant imaging-distance conjunction mode to the variable imaging-distance conjunction mode and vice versa according to the setting of the mode changeover switch. The process described above is realized, according to the selected mode, through the execution of specific program steps of a program stored in the storage unit 52.

It is advantageous to move the two-dimensional detection device 18 and the X-ray tube 16 in conjunction with each other based on the portion, which is to be imaged, of the subject. This will be described below.

A shift portion 28 (radiation source shift portion) mounted on the tube mounting portion 22 will be described with reference to FIGS. 3A and 3B. The shift process by the shift portion described below is the so-called active-side control mode.

In the present exemplary embodiment, the first sub-arm 15 and the second sub-arm 17 are connected to the frame of the C-arm 13 at the inside of the C-arm 13 via the first joint 19a and the second joint 19c. The first joint 19a and the second joint 19c rotate the first sub-arm 15 and the second sub-arm 17, respectively, so that the imaging distance (i.e., the distance between the detection device 18 and the X-ray tube 16) is changed. Therefore, since the first sub-arm 15 and the second sub-arm 17 move in the space between the two ends of the C-arm 13, even if the imaging distance is increased, the outer shape of the C-arm is not substantially increased.

However, the positional relationship between the line segment linking the X-ray tube 16 and the center of the two-dimensional detection device 18 and the C-arm 13 might be changed according to the change in the imaging distance.

Figure 3A:
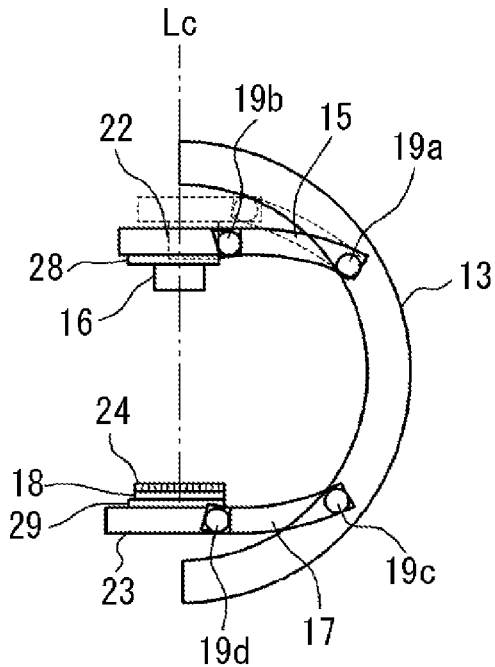
FIGS. 3A and 3B illustrate the movement of the X-ray tube by a shift unit.

As illustrated in FIG. 3A, the line segment linking the X-ray tube 16 and the center of the two-dimensional detection device 18 is defined as the imaging axis Lc with the state in which the first sub-arm 15 and the second sub-arm 17 are rotated to allow the X-ray tube 16 and the two-dimensional detection device 18 to be very close to each other. In the present exemplary embodiment, the imaging axis Lc is the same as the line linking both ends of the C-arm 13.

In the present exemplary embodiment, the X-ray tube 16 is arranged at the upper side, while the two-dimensional detection device 18 is arranged at the lower side as illustrated in FIG. 3A.

In the position illustrated in FIG. 3A, is assumed that the operator moves the first sub-arm 15 indicated by the solid line to be close to the frame of the C-arm 13, i.e., moves the sub-arm 15 indicated by the solid line to the position indicated by the broken line.

In this case, the first sub-arm 15 is rotated in the clockwise direction about the first joint 19a, so that the second joint 19b moves in the upper-right direction. Therefore, the center of the X-ray tube 16 moves to the right from the imaging axis Lc. Accordingly, the line segment linking the X-ray tube 16 and the center of the two-dimensional detection device 18 is shifted away from the imaging axis Lc, whereby the X-ray photography in the imaging range desired by the operator cannot be executed.

Figure 3B:
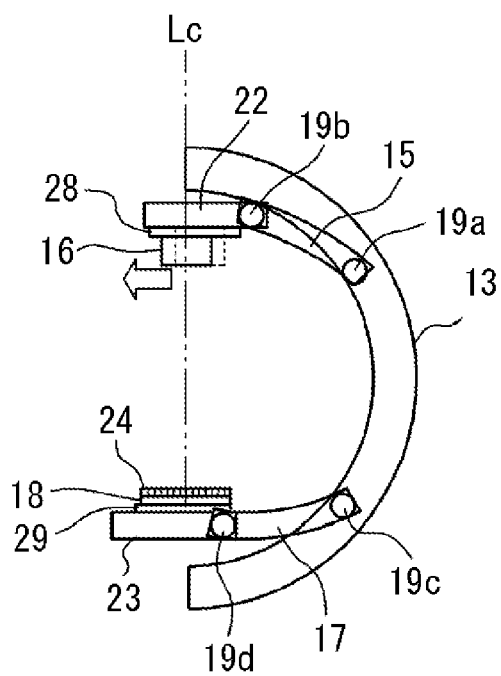

Accordingly, the X-ray tube 16 has to be shifted in the direction orthogonal to the imaging axis Lc, i.e., shifted to the left as illustrated by the arrow in FIG. 3B, to allow the line segment linking the X-ray tube 16 and the center of the two-dimensional detection device 18 to coincide with the imaging axis Lc.

The shift portion 28 has a function of shifting the X-ray tube 16 in the direction orthogonal to the imaging axis Lc and in the direction of the plane formed by the frame of the C-arm 13 to the tube mounting portion 22. The shift portion 28 is, for example, a ball screw or a linear-moving slide apparatus.

The shift portion 28 shifts the X-ray tube 16 in the direction toward the inside of the C-arm 13 when the imaging distance is decreased, while shifts the X-ray tube 16 in the direction toward the outside of the C-arm 13 when the imaging distance is increased. The shift amount of the shift portion 28 for shifting the X-ray tube 16 is calculated by the control unit 50.

Specifically, the control unit 50 detects the movement of the first sub-arm 15, i.e., the rotation angle of the first joint 19a, and calculates the shift amount according to the detected rotation angle. A correspondence table or the like is stored in the storage unit 52 beforehand, and the shift amount according to the rotation angle may be calculated based on the correspondence table by the control unit 50. In this manner, the shift portion 28 shifts the X-ray tube 16 orthogonal to the imaging axis Lc in accordance with the rotation angle of at least one of the joints 19a to 19d.

As described above, the shift portion 28 shifts the X-ray tube 16 based on the shift amount calculated by the control unit 50, thereby allowing the line segment linking the X-ray tube 16 and the center of the two-dimensional detection device 18 to agree with the imaging axis Lc as illustrated in FIG. 3B. Thus, the shift portion 28 can move the focal point of the X-ray tube 16 to the imaging axis Lc.

In the above description, the shift portion 28 shifts the X-ray tube 16. A shift portion (detection device shift portion) 29 similarly shifts the two-dimensional detection device 18 in the direction orthogonal to the imaging axis Lc.

The shift portion 29 shifts the two-dimensional detection device 18 in the direction toward the inside of the C-arm 13 when the imaging distance is decreased, while it shifts the two-dimensional detection device 18 in the direction toward the outside of the C-arm 13 when the imaging distance is increased. The shift amount of the shift portion 29 for shifting the two-dimensional detection device 18 is calculated by the control unit 50 in the same manner as described above in reference to the shift portion 28.

As described above, the shift portion 29 shifts the two-dimensional detection device 18 based on the shift amount calculated by the control unit 50, thereby allowing the line segment linking the X-ray tube 16 and the center of the two-dimensional detection device 18 to coincide with the imaging axis Lc. Thus, the shift portion 29 can move the center of the two-dimensional detection device 18 to the imaging axis Lc.

The operations of the shift portions 28 and 29 are different according to the set mode. Specifically, when the detection device mounting portion 23 is moved to change the imaging distance when the conjunction mode is set by the mode changeover switch described above, the first sub-arm 15 and the tube mounting portion 22 also move in conjunction with the detection device mounting portion 23. Therefore, the shift portion 29 shifts the two-dimensional detection device 18, while the shift portion 28 shifts the X-ray tube 16.

On the other hand, even if the detection device mounting portion 23 is moved to change the imaging distance when the single mode is set, the shift portion 29, which is at the moved side, only shifts the two-dimensional detection device 18.

In the above description, at least one of the X-ray tube 16 and the two-dimensional detection device 18 is shifted so that the center thereof can be aligned with the imaging axis Lc, which is the line segment linking the X-ray tube 16 and the center of the two-dimensional detection device 18. However, the present invention is not limited thereto.

Another shifting manner by the shift portions 28 and 29 will be described below. The shifting manner described below is the so-called passive-side control mode.

For example, when the operator moves the two-dimensional detection device 18, the center of the two-dimensional detection device 18 moves, so that a new imaging axis passing the center of the two-dimensional detection device 18 is passively determined. Therefore, the shift portion 28 at the X-ray tube 16 shifts the X-ray tube 16 to agree with the new imaging axis.

On the other hand, when the operator moves the X-ray tube 16, the center (focal point) of the X-ray tube 16 moves, so that a new imaging axis passing the center of the X-ray tube 16 is passively determined. Therefore, the shift portion 29 at the two-dimensional detection device 18 shifts the two-dimensional detection device 18 to agree with the new imaging axis.

The shift amount of the shift portions 28 and 29 for shifting the X-ray tube 16 or the two-dimensional detection device 18 is calculated by the control unit 50. Specifically, the control unit 50 detects the movement of the first sub-arm 15, i.e., the rotation angle of the first joint 19a, and calculates the position of the new imaging axis according to the detected rotation angle.

The control unit 50 further calculates the shift amount for shifting the two-dimensional detection device 18 that agrees with the calculated imaging axis. The shift portion 29 at the two-dimensional detection device 18 shifts the two-dimensional detection device 18 based on the calculated shift amount. On the other hand, when the second sub-arm 17 is moved, the control unit 50 calculates the shift amount of the X-ray tube 16.

The shift portion 28 at the X-ray tube 16 shifts the X-ray tube 16 based on the calculated shift amount. The process described above is realized by the execution of the program according to the mode stored in the storage unit 52.

As described above, in the so-called passive-side control mode, the X-ray tube 16 or the two-dimensional detection device 18 at the side moved by the operator is not automatically shifted. Therefore, the X-ray tube 16 or the two-dimensional detection device 18 is easily positioned.

In the above description, the shift portions 28 and 29 are mounted on the tube mounting portion 22 and the detection device mounting portion 23 respectively. However, the present invention is not limited thereto. Specifically, the shift portions 28 and 29 may optionally be configured, so long as they can move the X-ray tube 16 and the two-dimensional detection device 18 with respect to the respective sub-arms.

Figure 4A:
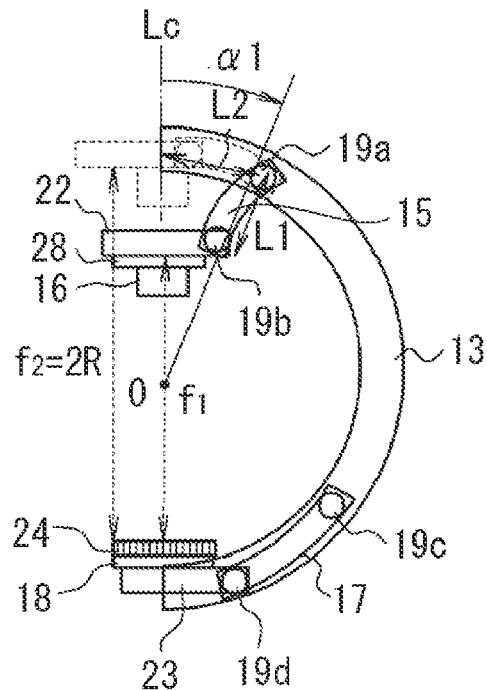
FIGS. 4A and 4B illustrate the position where a sub-arm is connected to a C-arm.

A preferable range of the position on the frame of the C-arm 13 where the first sub-arm 15 and the second sub-arm 17 are provided will next be described with reference to FIGS. 4A and 4B.

One of the factors for determining the positional range is the grid portion 24. When the convergent distance of the grid portion 24 is defined as f0, the limit of the usage distance of the grid portion 24 is set to include the convergent distance f0.

When the lower limit of the usage distance is defined as f1, and the upper limit of the usage distance is defined as f2, the equation of f1=<f0=<f2 is established. The limit of the usage distance f1=<f0=<f2 represents the range where the amount of cutting off the X-ray that is effective for the X-ray photography by the grid portion 24 is not more than a specified value. At the portion without the range described above, the subject is exposed to the radiation more than necessary, so that this range is not preferable for the X-ray photography.

The first sub-arm 15 and the second sub-arm 17 are generally desirable to be short. However, when they are too short, the interference problem between the X-ray tube 16 and the two-dimensional detection device 18 arises. Therefore, there are preferable ranges for the positions of the first joint 19a and the third joint 19c.

The factor for determining the range of the link position is the lower limit f1 of the usage distance. As illustrated in FIG. 4A, when the central point of the semicircular C-arm 13 is defined as O, the angle from the end portion of the C-arm 13 to the first joint 19a is defined as α1.

The end portion of the C-arm 13, in the present exemplary embodiment, is preferably aligned with the crossing portion where the imaging axis Lc linking the X-ray tube 16 and the center of the two-dimensional detection device 18 and the C-arm 13 cross or substantially cross. The position of the first joint 19a with the angle α1 is the position enabling the shortest sub-arm.

The angle α1 is set so that the distance L1 between the first joint 19a and the second joint 19b is equal to the distance L2 between the first joint 19a and the end portion of the C-arm 13. In the above description, the number of the joints between the first sub-arm 15 and the tube mounting portion 22 is one.

When there are plural joints, the distance between the first joint 19a and the joint farthest from the first joint 19a is defined as the distance L1.

When the distance from the central point O to one end portion of the C-arm 13 is defined as the radius R, the equation below is established.

$$L1 = L2 \tag{1}$$

$$2R = f1 + L1 \times \cos(\alpha 1) \tag{2}$$

Specifically, the angle α1 that sets the distance L1 of the shortest sub-arm for establishing the equations (1) and (2) is selected.

Next, an angle α2 that sets the longest sub-arm is specified. The limit when the sub-arm is set to be longest is specified by the usability of the C-arm 13. Specifically, when the first sub-arm 15 is unnecessarily long, the space in the frame of the C-arm 13, i.e., the arc space is reduced.

As the arc space formed by the C-arm 13 is decreased, the space occupied by the subject is decreased. In view of this, the angle α2 is specified by the equation described below from the relationship illustrated in FIG. 4B, supposing that the cross-section of the subject is a rectangle.

$$f1 = R \times (1 + \cos(\alpha 2)) \tag{3}$$

Consequently, when the angle from one end portion of the C-arm 13 to the first joint 19a is defined as α, the range where the first joint 19a can be provided is represented by α1≦α≦α2. In FIGS. 4A and 4B, the first sub-arm 15 is taken as an example. However, the range where the third joint 19c is provided is similarly specified for the second sub-arm 17 holding the two-dimensional detection device 18.

In the above description, the case in which only one of the sub-arms 15 and 17 move is described, since the lower limit f1 of the imaging distance can be realized by moving only one of the sub-arms 15 and 17 when the single mode is set.

As described above, the factor for regulating the range where the first joint 19a and the third joint 19c are provided is the lower limit f1 of the imaging distance of the usage distance. Specifically, when the lower limit f1 of the imaging distance of the grid portion 24, which is mounted on the front surface of the two-dimensional detection device 18, is changed, the range where the first joint 19a and the third joint 19c can be provided also changes.

Therefore, the X-ray imaging apparatus 100 can be configured such that the lower limit f1 of the imaging distance of the grid portion 24 can be input by the operator through the operation unit 54 on the main body 11. The control unit 50 calculates the position where the first joint 19a and the third joint 19c move along the frame of the C-arm 13 according to the input lower limit f1 of the imaging distance.

Figure 4B:
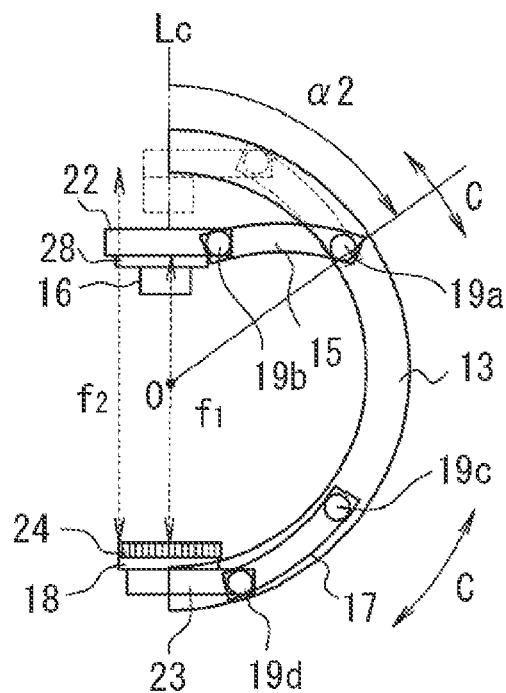

It may be configured so that the first joint 19a and the third joint 19c move along the frame of the C-arm 13 in the direction indicated by an arrow C in FIG. 4B to be located at the calculated position. The moving range of the unit to move the joints is restricted according to the range of the shifted distance by the shift portions 28 and 29.

In the above description, the mode is switched to the single mode or the conjunction mode by the mode changeover switch, and in the conjunction mode, the first sub-arm 15 and the second sub-arm 17 move in conjunction with each other.

The case in which the sub-arm is controlled based on imaged-portion information will next be described with reference to FIGS. 5A and 5B. The imaged portion indicates, for example, a patient's body part such as a spine, an abdomen, a head, four limbs (thigh, brachium, etc.), or the like. The control unit 50 acquires the imaged-portion information input by the operator through the operation unit 54 or receives the imaged-portion information according to Digital Imaging and Communications in Medicine (DICOM) standard from a network input unit (not illustrated).

The control unit 50 outputs the captured image data to the other external apparatus according to the DICOM standard.

Figure 5A:
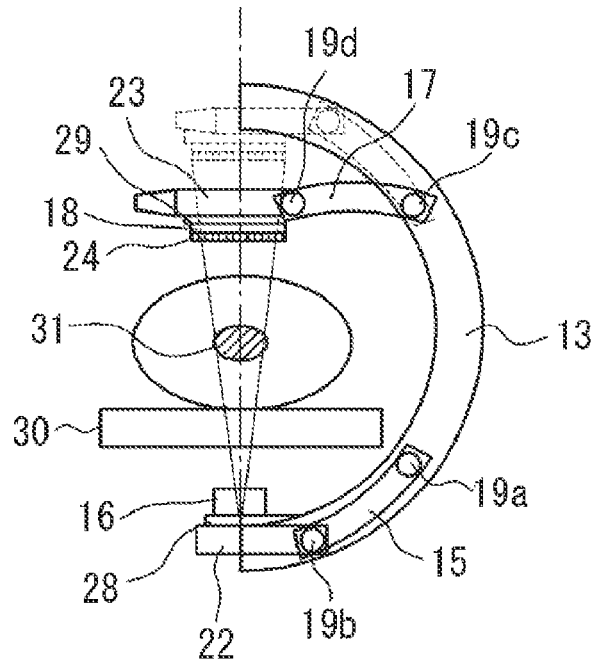
FIGS. 5A and 5B illustrate the case in which the sub-arms are moved in conjunction with each other according to a portion to be imaged.

It is supposed here that a spine is operated as an area of interest 31 of the subject as illustrated in FIG. 5A. In this case, even if the mode is set to the conjunction mode by the mode changeover switch, it is not preferable that the first sub-arm 15 and the second sub-arm 17 move in conjunction with each other, because there is no moving space.

Figure 5B:
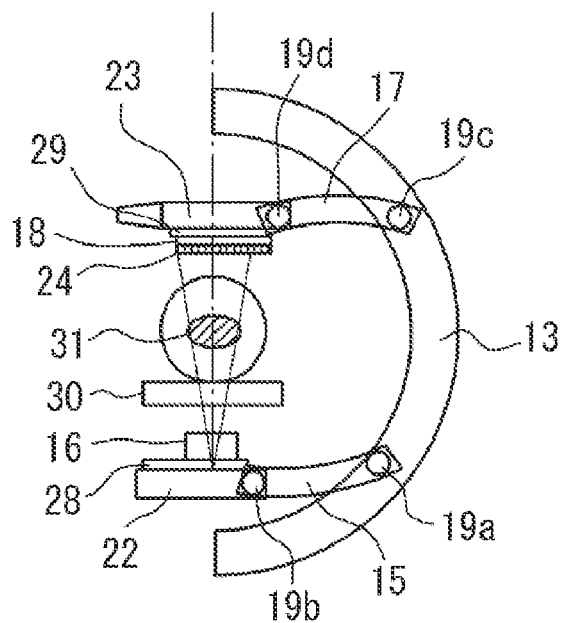

On the other hand, it is supposed here that a head is operated as the area of interest 31 of the subject as illustrated in FIG. 5B. In this case, when the mode is set to the conjunction mode by the mode changeover switch, it is preferable that the first sub-arm 15 and the second sub-arm 17 move in conjunction with each other because there is sufficient moving space around of the subject being imaged. As described above, it may be determined based on the imaged-portion information whether the first sub-arm 15 and the second sub-arm 17 move in conjunction with each other.

In the above description, when the lower limit f1 of the imaging distance of the grid portion 24 is changed, the first joint 19a and the third joint 19c move along the frame of the C-arm 13.

The case in which the first joint 19a and the third joint 19c move based on the imaged-portion information will be described below. It is supposed that the control unit 50 acquires the imaged-portion information, and determines that the imaged portion is the portion having a large sectional area, such as a spine or abdomen. In this case, at least either one of the first joint 19a and the third joint 19c move toward the end portion of the C-arm 13 along the frame of the C-arm 13 to increase the arc space of the C-arm 13 under the instruction from the control unit 50.

On the other hand, the control unit 50 may determine that the imaged portion is the portion having a small sectional area, such as four limbs. In this case, at least either one of the first joint 19a and the third joint 19c move toward the inside of the C-arm 13 along the frame of the C-arm 13 to decrease the arc space of the C-arm 13 under the instruction from the control unit 50.

As described above, the first joint 19a or the third joint 19c moves according to the imaged portion to move the first sub-arm 15 or the second sub-arm 17, whereby the arc space of the C-arm 13 according to the imaged portion can be changed.

The relationship between the arranging direction of lead plates that constitute the grid portion 24 and the direction of shifting the two-dimensional detection device 18 and the X-ray tube 16 by the shift portions 28 and 29 will next be described.

The grid portion 24 is formed by arranging plural lead plates (strips) with a predetermined space therebetween. Specifically, the arranging direction (hereinafter referred to as stripe direction) of the lead plates means the direction orthogonal to the direction in which the gaps between the lead plates are continued. In the present exemplary embodiment, the shift portions 28 and 29 shift the X-ray tube 16 or the two-dimensional detection device 18 in the direction orthogonal to the stripe direction of the grid portion 24.

Specifically, the shift portions 28 and 29 align the X-ray tube 16 or the two-dimensional detection device 18 in such a manner that the vertical line from the center of the two-dimensional detection device 18 passes through the center of the X-ray tube 16.

The lead plates of the grid portion 24 are arranged to be converged in the stripe direction. Therefore, when the alignment is shifted in the stripe direction, the cut-off of the X-ray is increased. Accordingly, the cut-off of the X-ray, which is effective for the diagnosis, is desensitized to the misalignment.

The respective units constituting the radiation imaging apparatus and the respective steps in the control process of the radiation imaging apparatus in the exemplary embodiment of the present invention can be realized by the execution of the program stored in the RAM or ROM of the control unit 50 (computer). The program and the computer-readable recording medium having the program recorded thereon are included in and make part of the present invention.

The present invention can be embodied in the form of a system, an apparatus, a method, a program, or a tangible non-transitory recording medium. Specifically, the present invention can applicable to an apparatus including one device or a plurality of devices.

The present invention supplies the program of software realizing the function of the above-mentioned exemplary embodiment directly to a system or an apparatus, or remotely to a system or an apparatus. The present invention includes the case in which the present invention is achieved by reading and executing the supplied program code by the computer in the system or the apparatus.

While the present invention has been described with reference to exemplary embodiments, it is to be understood that the invention is not limited to the disclosed exemplary embodiments. The scope of the following claims is to be accorded the broadest interpretation to encompass all modifications, equivalent structures, and functions.

This application claims priority from Japanese Patent Application Laid-Open No. 2009-133382 filed Jun. 2, 2009, which is hereby incorporated by reference herein in its entirety.

What is claimed is:

1. A radiation imaging apparatus comprising:
    a radiation source configured to irradiate a subject with radiation;
    a two-dimensional detection device configured to detect the radiation having passed through the subject;
    a grid portion configured to eliminate scattered rays of the radiation, which is mounted on an image-receiving surface of the two-dimensional detection device;
    an arm configured to arrange the radiation source and the two-dimensional detection device opposite to each other via a sub-arm that is rotatable connected to a frame of the arm at the inside from the end portion of the frame; and
    a shift unit configured to arrange at least one of the radiation source and the two-dimensional detection device in a direction orthogonal to a stripe direction of the grid portion to allow the radiation source to align with an imaging axis that links the radiation source with the two-dimensional detection device.

2. The radiation imagine apparatus according to claim 1, wherein the sub-arm comprises a first sub-arm and a second sub-arm,
    wherein the radiation source is arranged via the first sub-arm that is rotatably connected to the frame of the arm at the inside from one end portion of the frame, and
    wherein the two-dimensional detection device is arranged via the second sub-arm that is rotatably connected to the frame of the arm at the inside from the other end portion of the frame.

3. The radiation imaging apparatus according to claim 2,
wherein the shift unit comprises at least one radiation source shift unit, and
wherein the radiation source shift unit moves the radiation source according to the rotation of the first sub-arm to allow the radiation source to align with the imaging axis.

4. The radiation imaging apparatus according to claim 3,
wherein the radiation source shift unit moves the radiation source in the direction orthogonal to the stripe direction of the grid portion.

5. The radiation imaging apparatus according to claim 2,
wherein the shift unit comprises at least one detection device shift unit provided between the two-dimensional detection device and the second sub-arm, the detection device shift unit being configured to move the two-dimensional detection device towards the second sub-arm, and
wherein the detection device shift unit moves the two-dimensional detection device according to the rotation of the second sub-arm to allow the two-dimensional detection device to align with the imaging axis.

6. The radiation imaging apparatus according to claim 5,
wherein the detection device shift unit moves the two-dimensional detection device in the direction orthogonal to the stripe direction of the grid portion.

7. The radiation imaging apparatus according to claim 2, wherein either one of a connection portion between the first sub-arm and the arm and a connection portion between the second sub-arm and the arm move along the frame of the arm.

8. The radiation imaging apparatus according to claim 2, further comprising a conjunction unit configured to rotate the second sub-arm according to a rotation of the first sub-arm in conjunction with the first sub-arm or a conjunction unit configured to rotate the first sub-arm according to rotation of the second sub-arm in conjunction with the second sub-arm.

9. The radiation imaging apparatus according to claim 8, further comprising an input unit configured to input imaged-portion information,
wherein the conjunction unit moves the first sub-arm or the second sub-arm in conjunction with the second sub-arm or the first sub-arm based on the imaged-portion information input by the input unit.

10. A radiation imaging apparatus comprising:
a radiation source configured to irradiate a subject with radiation;
a two-dimensional detection device configured to detect the radiation having passed through the subject; and
a grid portion configured to eliminate scattered rays of the radiation, which is mounted on an image-receiving surface of the two-dimensional detection device,
wherein the radiation source is arranged via a first sub-arm that is rotatably connected to a frame of an arm at the inside from one end portion of the frame,
a radiation source shift unit, which is provided between the radiation source and the first sub-arm, configured to move the radiation source to the first sub-arm,
wherein the radiation source shift unit moves the radiation source in the direction orthogonal to a stripe direction of a grid portion of the two-dimensional detection device to allow the radiation source to align with the imaging axis passing through the center of the two-dimensional detection device changed by the movement of the second sub-arm.

11. A radiation imaging comprising:
a radiation source configured to irradiate a subject with radiation;
a two-dimensional detection device configured to detect the radiation having passed through the subject; and
a grid portion configured to eliminate scattered rays of the radiation, which is mounted on an image-receiving surface of the two-dimensional detection device,
wherein the radiation source is arranged via a first sub-arm that is rotatably connected to a frame of an arm at the inside from one end portion of the frame,
wherein the frame of the arm is a semicircular frame having a central point located along an imaging axis,
wherein, when an angle $\alpha$ from a crossing portion of the imaging axis, which links the two-dimensional detection device and the radiation source, and the arm to the connection portion between the first sub-arm and the arm or to the connection portion between the second sub-arm and the arm at the central point of the semicircular frame of the arm is defined as $\alpha$, the inequality of $\alpha 1 =< \alpha =< \alpha 2$ is established, and
when a lower limit of an imaging distance due to the grid portion, which is provided on the image-receiving surface of the two-dimensional detection device to eliminate the scattered rays of the radiation, is defined as f1, the radius of the semicircular frame of the arm is defined as R, the distance from the connection portion between the sub-arm and the arm to the connection portion between the sub-arm and the two-dimensional detection device or the radiation source is defined as L1, L1 is defined as a smallest value satisfying the following equations (1) and (2) below, and the distance from the connection portion between the sub-arm and the arm to the crossing portion is defined as L2, the equations of:

$$L1 = L2 \quad (1)$$

$$2R = f1 + L1 \times \cos(\alpha 1) \quad (2)$$

$$f1 = R \times (1 + \cos(\alpha 2)) \quad (3)$$

are satisfied.

12. A control method in a radiation imaging apparatus that includes:
a radiation source configured to irradiate a subject with radiation;
a two-dimensional detection device configured to detect the radiation having passed through the subject;
a grid portion configured to eliminate scattered rays of the radiation, which is mounted on an image-receiving surface of the two-dimensional detection device,
wherein the radiation source and the two-dimensional detection device are arranged to face each other across a C-arm, wherein the radiation source is arranged via a first sub-arm that is rotatably connected to the frame of the arm at the inside from one end portion of the frame, and the two-dimensional detection device is arranged via a second sub-arm that is rotatably connected to the frame of the arm at the inside from the other end portion of the frame,
a radiation source shift unit, which is provided between the radiation source and the first sub-arm, configured to move the radiation source to the first sub-arm, and
a detection device shift unit, which is provided between the two-dimensional detection device and the second sub-arm, configured to move the two-dimensional detection device to the second sub-arm, the method comprising:

shifting the radiation source by the radiation source shift unit, according to rotation of the first sub-arm, to move the radiation source in the direction orthogonal to a stripe direction of the grid portion to allow the radiation source to align with an imaging axis linking the radiation source and the two-dimensional detection device, or shifting the two-dimensional detection device by the detection device shift unit, according to rotation of the second sub-arm, to move the two-dimensional detection device in the direction orthogonal to a stripe direction of the grid portion to allow the two-dimensional detection device to align with an imaging axis linking the two-dimensional detection and the radiation source.

13. A non-transitory computer-readable storage medium storing a program that controls a radiation imaging apparatus that includes:

a radiation source configured to irradiate a subject with radiation;

a two-dimensional detection device configured to detect the radiation having passed through the subject;

a grid portion configured to eliminate scattered rays of the radiation, which is mounted on an image-receiving surface of the two-dimensional detection device, wherein the radiation source and the two-dimensional detection device are arranged to face each other across a C-arm, wherein the radiation source is arranged via a first sub-arm that is rotatably connected to the frame of the C-arm at the inside from one end portion of the frame, and the two-dimensional detection device is arranged via a second sub-arm that is rotatably connected to the frame of the C-arm at the inside from the other end portion of the frame, a radiation source shift unit, which is provided between the radiation source and the first sub-arm, configured to move the radiation source to the first sub-arm, and a detection device shift unit, which is provided between the two-dimensional detection device and the second sub-arm, configured to move the two-dimensional detection device to the second sub-arm, the program comprising:

computer-executable instructions for shifting the radiation source by the radiation source shift unit, according to rotation of the first sub-arm, to move the radiation source to align with an imaging axis linking the radiation source and the two-dimensional detection device, or computer-executable instructions for shifting the two-dimensional detection device by the detection device shift unit, according to rotation of the second sub-arm, to move the two-dimensional detection device in the direction orthogonal to a stripe direction of the grid portion to allow the two-dimensional detection device to align with an imaging axis linking the two-dimensional detection device and the radiation source.

\* \* \* \* \*